US00RE42260E

(19) United States
(12) Reissued Patent
Ramin et al.

(10) Patent Number: US RE42,260 E
(45) Date of Reissued Patent: Mar. 29, 2011

(54) COMPOSITION AND PROCESS FOR MAKING UP KERATIN SUBSTANCES

(75) Inventors: Roland Ramin, Paris (FR); Ingrid Brenne, L'Hay-les-Roses (FR)

(73) Assignee: L'Oreal S.A., Paris (FR)

(21) Appl. No.: 10/919,516

(22) Filed: Aug. 17, 2004

Related U.S. Patent Documents

Reissue of:
(64) Patent No.: 6,491,932
Issued: Dec. 10, 2002
Appl. No.: 09/655,841
Filed: Sep. 6, 2000

(30) Foreign Application Priority Data

Sep. 7, 1999 (FR) ..... 99 11174

(51) Int. Cl.
*A61K 6/00* (2006.01)

(52) U.S. Cl. ..... 424/61; 424/63; 424/70.7; 424/401

(58) Field of Classification Search ..... None
See application file for complete search history.

(56) References Cited

U.S. PATENT DOCUMENTS

| | | | | |
|---|---|---|---|---|
| 3,053,683 | A | 9/1962 | Yolles | |
| 5,201,929 | A | 4/1993 | Mizuno et al. | |
| 5,294,237 | A | 3/1994 | Mizuno et al. | |
| 5,624,486 | A * | 4/1997 | Schmid et al. | 106/404 |
| 6,004,567 | A | 12/1999 | Marchi-Lemann et al. | |
| 6,451,294 | B1 | 9/2002 | Simon | |
| 6,491,932 | B1 * | 12/2002 | Ramin et al. | 424/401 |
| 6,630,018 | B2 | 10/2003 | Bauer et al. | |
| 6,632,275 | B1 | 10/2003 | Schoen et al. | |

FOREIGN PATENT DOCUMENTS

| | | | |
|---|---|---|---|
| EP | 0 327 739 | * | 8/1989 |
| EP | 0 665 004 | * | 8/1995 |
| EP | 0 723 997 | | 7/1996 |
| EP | 0 608 388 B1 | | 7/1998 |
| EP | 1 064 918 | | 1/2001 |
| EP | 1 082 952 | | 10/2002 |
| JP | 61-229808 | | 10/1986 |
| JP | 62-108805 | | 5/1987 |
| JP | 1-208324 | | 8/1989 |
| JP | 1-215865 | | 8/1989 |
| JP | 3-239769 | | 10/1991 |
| JP | 4-37622 | | 2/1992 |
| JP | 5-17710 | * | 1/1993 |
| JP | 6-116507 | | 4/1994 |
| JP | 6-40576 | | 10/1994 |
| JP | 7-258460 | * | 10/1995 |
| JP | 9-71417 | | 3/1997 |
| JP | 9-188830 | * | 7/1997 |
| JP | 09-263519 | | 10/1997 |
| JP | 10-316883 | | 2/1998 |
| JP | 10-158450 | * | 6/1998 |
| JP | 10-158541 | * | 6/1998 |
| JP | 10-259316 | | 9/1998 |
| JP | 10-330658 | | 12/1998 |
| JP | 2001-11340 | | 6/2001 |
| WO | WO 93/08237 | | 10/1992 |
| WO | WO 99/61529 | | 12/1999 |
| WO | WO 00/78282 | | 12/2000 |
| WO | WO 01/18126 | | 3/2001 |

OTHER PUBLICATIONS

Patent Abstracts of Japan, vol. 012, No. 372, Oct. 5, 1998 (JP 63 122616).*
English language Derwent Abstract of JP 5–177710.*
English language Derwent Abstract of JP 9–188830.*
English language Derwent Abstract of Jp 10–15841.*
Patent Abstracts of Japan, vol. 015, No. 332, Aug. 23, 1991 (JP 03 127708).*
English language Derwent Abstract of JP 7–258460.*
English language Derwent Abstract of JP 10–158450.*
*38th FRP CON–EX '93*, pp. 39–42 (1993).
Decision of European Patent Office Opposition Division for EP 1 082 952, dated Jan. 13, 2005.
*Handbook for Color Material Engineering*, pp. 303–306 & 1305–1309 (Asakura Shoten 1989).
Letter from L'Oréal to Opposition Division of European Patent Office regarding Opposition of EP 1 082 952 B1, dated Sep. 17, 2004.
L'Oréal Response to European Patent Office in Application No. 00 402 186.1–2114, dated Jan. 10, 2002.
Machine and Partial Translations of HP 9–188830.
Machine and Partial Translations of JP 10–158541.
Material Safety Data Sheet for "Glass Flake Covered with Metal GF 2525" by Toyo Aluminum K.K. (1998).
Official Report of the Oral Procedure in Front of the Opposition Division, for Opposition of EP 1 082 952, dated Jan. 13, 2005.
Partial Translation of JP 3–239769.
Partial Translation of JP 6–116507.
Partial Translation of JP 7–258460.
Preliminary Report from the Oral Proceedings in Opposition of EP 1 082 952 B1, dated Jan. 20, 2004.
Response to First Appeal in Opposition of EP 1 082 952 B1, filed by L'Oréal on Nov. 29, 2005.
Specification Sheet for "Crystal Star GF 550" sold by Toyal Europe (1997).
Specification Sheet for "GF 2525" sold by Toyal Europe (1998).
Specification Sheet for "GF 2140" sold by Toyal Europe (1998).
Specification Sheet for "Microglas Metashine Refax 2025PS (8011)" sold by Toyal Europe (1998).

(Continued)

*Primary Examiner*—Carlos A. Azpuru
(74) *Attorney, Agent, or Firm*—Finnegan, Henderson, Farabow, Garrett & Dunner, L.L.P.

(57) ABSTRACT

A cosmetic make-up composition comprising, in a cosmetically acceptable medium, a dyestuff comprising glass particles coated with at least one metallic coat. The invention also relates to a cosmetic process for making up keratin substances. The make-up obtained can have a sparkling and wear-resistant metallic appearance.

50 Claims, No Drawings

OTHER PUBLICATIONS

"Substantiation of Appeal" filed by Nippon Sheet Glass Co., Ltd. In Opposition of EP 1 082 952 B1.

Translation of JP 61–229808.

Translation of JP 62–108805.

Translation of 38th FRP CON–EX '93.

Entry for "Mica" in *The Penguin Dictionary of Science* (6th ed., 1986).

Notice of Opposition to a European Patent filed Apr. 2, 2003 by Nippon Sheet Glass Co., Ltd.

Notice of Opposition to a European patent filed Apr. 10, 2003 by Atsushi Ito.

Opposition Amendment by L'Oréal filed Nov. 17, 2003.

Summons to Attend Oral Proceedings and Preliminary Opinion by EPO Opposition Division dated Feb. 25, 2004.

Response to Summons to Attend Oral Proceedings filed Sep. 14, 2004 by Nippon Glass.

European Opposition Proceedings and Appeal for EP 1 082 952, filed on Apr. 2, 2003, by Nippon Sheet Glass Co., Ltd., and on Apr. 10, 2003, by Atsushi Ito.

* cited by examiner

COMPOSITION AND PROCESS FOR MAKING UP KERATIN SUBSTANCES

Matter enclosed in heavy brackets [ ] appears in the original patent but forms no part of this reissue specification; matter printed in italics indicates the additions made by reissue.

The present invention relates to a cosmetic composition for making up at least one keratin substance, comprising at least one treated glass particle. The invention also relates to a cosmetic process for making up at least one keratin substance. The composition according to the invention can be applied to the nails, facial or body skin, including the lips, the eyelashes, and the hair, in particular of human beings. More specifically, the invention can be a nail varnish.

The make-up composition can be a nail varnish, a face powder, an eyeshadow, a foundation, a mascara, an eyeliner, or a make-up product for the lips or body. The composition can also be applied to make-up accessories such as false nails, false eyelashes or wigs, or alternatively to pastilles or patches adhering to the skin or the lips (such as beauty spots).

Make-up compositions, such as nail varnishes, are colored with the aid of dyestuffs such as soluble dyes, pigments that are generally metal oxides, such as iron oxides, or alternatively with the aid of nacres such as micas coated with metal oxides such as titanium oxide. However, when the film of make-up is subjected to stresses such as impacts, pressure or rubbing, the dyestuffs and in particular the pigments are not always resistant to these stresses and wear away. A substantial loss of color of the make-up is then observed, thus obliging the user to reapply the make-up regularly, optionally after the damaged coat has been removed. It is also known practice to use aluminum flakes to obtain a color with a metallic effect. Like the pigment, these flakes can show little resistance to stresses and wear away. Furthermore, these flakes can be light-opaque, light-scattering, and matte. In addition, when they are combined with colored pigments which do not have a metallic appearance, for example nacres, the color of these pigments may not emerge; it is therefore not possible to obtain a make-up having a colored metallic appearance.

It would be advantageous to overcome at lest one of the drawbacks mentioned above and one of the embodiments of the invention relates to obtaining a make-up on at least one keratin substance that has a sparkling metallic appearance and good wear resistance.

The inventors have observed that a novel type of make-up for at least one keratin substance can be obtained by using a cosmetic composition comprising at least one dyestuff in a cosmetically acceptable medium, wherein the at least one dyestuff comprises glass particles coated with at least one metallic coat.

When the composition according to the invention is applied to at least one keratin substance such as the nails, the glass particles coated with at least one metallic coat can be distributed in the coat deposited. This composition can afford a make-up film which has a very shiny, sparkling metallic appearance, with a mirror effect, irrespective of the direction of observation, and which does not scatter light. The make-up can also have good wear resistance, in particular, resistance to impacts, rubbing and abrasion, as well as good resistance to chipping. A sparkling make-up which adheres well to the made-up support and which has good staying power can, in certain embodiments of the invention, be obtained. Furthermore, the glass particles can transmit light well, which allows the glass particles to be combined with at least one colored pigment in order to obtain colored make-up with a metallic effect.

Another subject of the invention is a cosmetic process for making up at least one keratin substance, comprising the application of a composition as defined above to the at least one keratin substance.

Another subject of the invention is also the use, in a composition for making up at least one keratin substance, of glass particles coated with at least one metallic coat, in order to obtain a glossy and/or wear-resistant make-up.

The glass particles used as the at least one dyestuff in the composition according to the invention are coated with at least one metallic coat.

The at least one metallic coat can be formed from at least one metal, such as silver, aluminum, chromium, nickel, molybdenum, gold, copper, tin, and magnesium, and, among these representative examples, silver, chromium, nickel, and molybdenum.

In one embodiment of the invention, the at least one metallic coat of the coated glass particles can be present in an amount by weight, relative to the total weight of the particles, generally ranging from 0.1% to 50%, such as 1% to 20%, and further such as 2% to 8%.

The glass particles coated with the at least one metallic coat can have an average size generally ranging from 1 μm to 500 μm, such as 10 μm to 300 μm, and further such as 25 μm to 150 μm.

The glass particles coated with the at least one metallic coat can have a thickness generally ranging from 0.1 μm to 25 μm, such as 0.5 μm to 10 μm, and further such as 0.5 μm to 5 μm.

The glass particles coated with the at least one metallic coat are described in particular in documents JP-A-09 188 830, JP-A-10 158 450, JP-A-10 158 541, JP-A-07 25 258 460 and JP-A-05 017 710, the disclosures of which are specifically incorporated by reference herein.

The glass particles coated with the at least one metallic coat that can be used, for example, are sold by the company Toyal under the names Microglass Metashine REFSX 2025 PS and GF 2140, silver-coated particles, and under the names Crystal Star GF 550 and GF 2525, particles coated with a nickel/chromium/molybdenum alloy.

The glass particles coated with the at least one metallic coat can be present in the composition according to the invention in an amount by weight, relative to the total weight of the composition, generally ranging from 0.1% to 90%, such as 1% to 30%, and further such as 2% to 10%.

The composition according to the invention can also comprise at least one film-forming polymer. In the present application, the expression "film-forming polymer" means a polymer which is capable, by itself or in the presence of a film-forming auxiliary, of forming an isolable film. The at least one film-forming polymer in the composition can be dissolved or disposed in the form of particles in the cosmetically-acceptable medium of the composition according to the invention.

Representative film-forming polymers that can be used in the composition of the present invention include synthetic polymers, radical-mediated types, polycondensate types, and polymers of natural origin.

The expression "radical-mediated film-forming polymer" means a polymer obtained by polymerization of one or more monomers containing unsaturation, in particular ethylenic unsaturation, certain monomers being capable of homopolymerizing (unlike polycondensate).

The at least one film-forming polymer of radical-mediated type can be chosen from vinyl polymers, and vinyl copolymers, in particular acrylic polymers.

The vinyl film-forming polymers can result from the polymerization of monomers containing ethlenic unsaturation having at least one acid group and/or esters of these acidic monomers and/or amides of these acidic monomers.

Representative monomers bearing an acid group which can be used include α,β-ethylenic unsaturated carboxylic acids, such as acrylic acid, methacrylic acid, crotonic acid, maleic acid and itaconic acid, and, in particular, (meth) acrylic acid and crotonic acid. Among these representative monomers, (meth)acrylic acid can be used.

Representative esters of acid monomers include (meth) acrylic acid esters, also known as (meth)acrylates, especially alkyl(meth)acrylates, in particular of a $C_1$–$C_{20}$ alkyl, such as $C_1$–$C_8$ alkyl; aryl(meth)acrylates, in particular of a $C_6$–$C_{10}$ aryl; and hydroxyalkyl(meth)acrylates, in particular of a $C_2$–$C_6$ hydroxyalkyl.

Representative alkyl(meth)acrylates include methyl methacrylate, ethyl methacrylate, butyl methacrylate, isobutyl methacrylate, 2-ethylhexyl methacrylate and lauryl methacrylate.

Representative hydroxyalkyl(meth)acrylates include hydroxyethyl acrylate, 2-hydroxypropyl acrylate, hydroxyethyl methacrylate and 2-hydroxypropyl methacrylate.

Representative aryl(meth)acrylates include benzyl acrylate and phenyl acrylate.

Among all these representative examples, the (meth) acrylic acid esters may be the alkyl(meth)acrylates.

According to the present invention, the alkyl group of the esters may be substituted, such as fluorinated or perfluorinated, i.e., some or all of the hydrogen atoms in the alkyl group are substituted with fluorine atoms.

Representative amides of the acid monomers include (meth)acrylamides, and especially N-alkyl(meth) acrylamides, in particular of a $C_2$–$C_{12}$ alyl. Representative N-alkyl(meth)acrylamides include N-ethylacrylamide, N-t-butylacrylamide and N-t-octylacrylamide.

The vinyl film-forming polymers can also result from the homopolymerization or copolymerization of at least one monomer chosen from vinyl esters and styrene monomers. In particular, these monomers can be polymerized with acid monomers and/or esters thereof and/or amides thereof, such as those mentioned above.

Representative vinyl esters include vinyl acetate, vinyl neodecanoate, vinyl pivalate, vinyl benzoate and vinyl t-butylbenzoate.

Styrene monomers which may be mentioned are styrene and α-methylstyrene.

The list of monomers given is not limiting and it is possible to use any monomer known to those skilled in the art which falls within the categories of acrylic and vinyl monomers (including monomers modified with a silicone chain).

Representative acrylic film-forming polymers in aqueous dispersion which can be used according to the invention include those sold by the company Zeneca under the names Neocryl XK-90®, Neocryl A-1070®, Neocryl A-1090®, Neocryl BT-62®, Neocryl A-1079® and Neocryl A-523®, and those sold by the company Dow Chemical under the name Dow Latex 432®.

Polycondensates which can be used as the at least one film-forming polymer can be anionic, cationic, nonionic or amphoteric and are chosen from polyurethanes, polyurethane-acrylics, polyurethane-polyvinylpyrrolidones, polyester-polyurethanes, polyether-polyurethanes, polyureas and polyurea-polyurethanes.

Representative film-forming polyurethanes can be, for example, aliphatic, cycloaliphatic or aromatic polyurethanes, polyurea-urethanes or polyurea copolymers, comprising:

at least one sequence originating from monomers chosen from aliphatic monomers, cycloaliphatic monomers, aromatic polyester monomers, branched and non-branched silicone monomers, such as polydimethylsiloxane and polymethylphenylsiloxane, and monomers comprising fluoro groups.

Representative film-forming polyurethane polymers in aqueous dispersion, according to the invention, include polyester-polyurethanes sold under the names "Avalure UR-405®", "Avalure UR-410®", "Avalure UR425®", "Avalure UR-450®" and "Sancure 2060®" by the company Goodrich and the polyether-polyurethanes sold under the names "Sancure 878®" by the company Goodrich and "Neorez R 970®" by the company Zeneca.

Representative film-forming polycondensates include polyesters, polysteramides, fatty-chain polyesters, polyamides and epoxyester resins, resins resulting from the condensation of formaldehyde with an arylsulphonamide, and arylsulphonamide epoxy resins.

The polyesters can be obtained, in a known manner, by polycondensation of dicarboxylic acids with polyols, in particular diols.

The dicarboxylic acid can be aliphatic, alicyclic or aromatic. Representative acids include oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioc acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalene-dicarboxylic acid. These dicarboxylic acid monomers can be used alone or in combinations of at least two dicarboxylic acid monomers. Phthalic acid, isophthalic acid, and terephthalic acid can be chosen from among the representative acids.

Representative diols can be chosen from aliphatic, alicyclic, and aromatic diols, such as ethylene glycol, diethylene glycol, triethylene glycol, 1,3-propanediol, cyclohexanedimethanol, and 4-butanediol. Other representative polyols include glycerol, pentaerylthritol, sorbitol, and trimethylolpropane.

The polyesteramides can be obtained in a similar manner to the polyesters by polycondensation of diacids with diamines or with amino alcohols. Representative diamines include ethylenediamine, hexamethylenediamine, and meta- and para-pheylene-diamine. A representative amino acid alcohol is monoethanolamine.

The polyester can also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$, or $Fe^{3+}$ ion. A difunctional aromatic monomer comprising such a group —$SO_3M$ is representative.

The aromatic nucleus of the difunctional aromatic monomer also bearing a group —$SO_3M$ as described above can be chosen, for example, from benzene, naphthalene, anthracene, diphenyl, oxydiphenyl, sulphonyidiphenyl, and methylenediphenyl nuclei. Examples of difunctional aromatic monomers also bearing a group —$SO_3M$ include sulpho-isophthalic acid, sulphoterephthalic acid, sulphophthalic acid, and 4-sulphonaphthalene-2,7-dicarboxylic acid.

Copolymers based on isophthalate/sulphoisophthalate, and more particularly copolymers obtained by condensation of diethylene glycol, cyclohexanedimethanol, isophthalic acid, and sulphoisophthalic acid, can be used in the compositions forming the subject of the invention. Such polymers are sold, for example, under the brand name Eastman AQ by the company Eastman Chemical Products.

Representative optionally modified polymers of natural origin include shellac resins, sandaraque gums, dammar resins, elemis gums, copal resins, and cellulose polymers, such as nitrocellulose, cellulose acetate, cellulose acetobutyrate, cellulose acetopropionate, and ethylcellulose.

The at least one film-forming polymer can be present in the composition according to the invention in an amount, by weight, relative to the total weight of the composition, generally ranging from 1% to 70%, such as 10% to 40%.

According to the invention, the composition comprises a cosmetically-acceptable medium, wherein the medium is chosen from at least one solvent and water. The at least one solvent can be representatively chosen from organic solvents. The at least one solvent can be representatively chosen from aqueous-alcoholic mixtures, such as those comprising at least one $C_1$–$C_5$ monoalcohol.

Representative organic solvents include:

- ketones that are liquid at room temperature, such as methyl ethyl ketone, methyl isobutyl ketone, diisobutyl ketone, isophorone, cyclohexanone, and acetone;
- alcohols that are liquid at room temperature, such as ethanol, isopropanol, diacetone alcohol, 2-butoxyethanol, and cyclohexanol;
- glycols that are liquid at room temperature, such as ethylene glycol, propylene glycol, pentylene glycol, and glycerol;
- propylene glycol ethers that are liquid at room temperature, such as propylene glycol monomethyl ether, propylene glycol monomethyl ether acetate, and dipropylene glycol mono-n-butyl ether;
- short-chain esters, containing from 3 to 8 carbon atoms in total, such as ethyl acetate, methyl acetate, propyl acetate, n-butyl acetate, and isopenyl acetate;
- ethers that are liquid at room temperature, such as diethyl ether, dimethyl ether, or dichlorodiethyl ether;
- alkanes that are liquid at room temperature, such as decane, heptane, dodecane, and cyclohexane;
- cyclic aromatic compounds that are liquid at room temperature, such as toluene and xylene; or
- aldehydes that are liquid at room temperature, such as benzaldehyde and acetaldehyde.

These solvents are more particularly suitable for nail make-up: the composition thus constitutes a nail varnish.

The solvent content by weight, relative to the total weight of the composition, can generally range from 30% to 99%, such as 60% to 90%.

To improve the film-forming properties of the composition, in particular of the base and/or surface composition according to the invention, at least one film-forming auxiliary agent may be provided.

When the at least one film-forming auxiliary agent is used with the at least one film-forming polymer, the at least one film-forming auxiliary agent can be chosen from any compound known to those skilled in the art as being capable of fulfilling the desired function, and can be chosen in particular from plasticizers.

In addition, when the composition comprises the at least one film-forming polymer in the form of particles dispersed in the corresponding medium of the composition, the at least one film-forming auxiliary agent can also be chosen from coalescers.

The composition according to the invention can also comprise at least one additional dyestuff, other than the at least one glass particles described previously. Representative additional dyestuffs can include dyes (water-soluble or liposoluble) and pulverulent dyestuffs, such as pigments, nacres, and flakes that are well-known to those skilled in the art. The at least one additional dyestuff can be present in the composition in an amount measured by weight, relative to the total weight of the composition, generally ranging from 0.01% to 50%, such as 0.01% to 30%.

The composition according to the invention can also comprise at least one additive known to those skilled in the art as being capable of being incorporated into such a composition. Representative additives include thickeners, fillers, spreading agents, wetting agents, dispersants, anti-foaming agents, preserving agents, UV screening agents, active agents, surfactants, moisturizers, fragrances, neutralizing agents, stabilizers, and antioxidants. A person skilled in the art should take care to select the at least one additive and/or the amount thereof, such that the advantageous properties of the corresponding composition according to the invention are not, or are not substantially, adversely affected by the addition envisaged.

The composition according to the invention can be prepared by a person skilled in the art on the basis of his general knowledge and according to the prior art.

The invention is illustrated in greater detail in the examples which follow.

EXAMPLE 1

A nail varnish having the composition below was prepared:

| | |
|---|---|
| Nitrocellulose | 10 g |
| Plasticizers and resin | 15 g |
| Rheological agent | 1.5 g |
| Silver-coated glass particles (GF 2140 from the company Toyal) | 10 g |
| Ethyl acetate, butyl acetate qs | 100 g |

After applying the composition to the nails, a make-up film with a very glossy metallic appearance was obtained. The make-up shows good wear resistance.

EXAMPLE 2

A nail varnish having the composition below was prepared:

| | |
|---|---|
| Nitrocellulose | 10 g |
| Plasticizers and resin | 15 g |
| Rheological agent | 1.5 g |
| Glass particles coated with nickel/chromium/molybdenum alloy (Crystal Star GF 550 from the company Toyal) | 5 g |
| Red pigment | 0.5 g |
| Ethyl acetate, butyl acetate qs | 100 g |

The composition is applied to the nails. A red make-up with a sparkling metallic appearance is obtained.

EXAMPLES 3 TO 5 (Comparative)

Two nail varnishes according to the invention (Examples 3 and 4) and a nail varnish not forming part of the invention (Example 5) were prepared according to the following compositions, the content being given in grams:

| Ingredient | Example 3 | Example 4 | Example 5 |
|---|---|---|---|
| Nitrocellulose | 11 | 11 | 11 |
| Tosylamide/formaldehyde copolymer | 10.1 | 10.1 | 10.1 |
| Bentonite | 1.1 | 1.1 | 1.1 |
| Tributyl acetyl citrate | 6.7 | 6.7 | 6.7 |
| Isopropyl alcohol | 7.9 | 7.9 | 7.9 |
| Pigment (1) | 10 | — | — |
| Pigment (2) | — | 10 | — |
| Aluminium powder (3) | — | — | 10 |
| Ethyl acetate | 22 | 22 | 22 |
| Butyl acetate | 39.2 | 39.2 | 39.2 |

(1): Silver-coated glass particles sold under the name GF 2140 by the company Toyal (2): Silver-coated glass particles sold under the name Microglass Metashine REFSX 2025PS by the company Toyal (3): Aluminum powder sold under the name Silver ET 1630 by the company Silberline a) Wear-resistance Test The wear resistance of the films was measured according to AFNOR standard NF T 30-015. Each composition was applied in the form of a coat 600 mm thick (before drying) onto a disc and then left to dry for 1 hour at 30° C. The film of varnish deposited on the disc was then placed for 1 hour in contact with abrasive discs (Taber abrasimeter), the disc making a complete rotation in one second. After 1 hour, the disc was weighed and the loss of mass LM of product, expressed as a percentage of the weight lost relative to the initial weight, was calculated.

The following results were obtained:

| | |
|---|---|
| LM=3.58% | Example 3 |
| LM=4.98% | Example 4 |
| LM=5.99% | Example 5 |

It is seen that compositions 3 and 4 according to the invention have better abrasion strength than composition 5.

b) Light-reflection Test

The test compositions contained 5% by weight of pigment (1), (2) or (3), respectively, instead of 10%.

For each composition, a coat 300 μm thick (before drying) was deposited on a glass plate and, after drying for 24 hours at room temperature, the light-reflecting properties of the film of varnish were then determined.

The film was lit with a light beam 1 cm in diameter inclined at an angle of 30° relative to the normal to the plane of the glass plate, and the amount of light reflected as a function of the angle was then measured using a variable-angle 10 photogoniometer.

For each composition, the reflection curve had the following characteristics:

| | Example 3 | Example 4 | Example 5 |
|---|---|---|---|
| Peak maximum (in arbitrary units, at the specular angle −30°) | 253.7 | 451.6 | 173.1 |
| Width at mid-height (in ° of angle) | 12.5 | 14 | 21 |

It is seen that the reflection curves for the films obtained with the compositions of Examples 3 and 4 according to the invention have a higher maximum and a narrower width at mid-height that the reflection curve for the film of Example 5. The films of Examples 3 and 4 thus reflect light much more than the film of Example 5. In addition, the films of Examples 3 and 4 scatter light less than the film of Example 5, because the divergence of the reflected beam is lower for the films of Examples 3 and 4 than that for the film of Example 5. The coated glass particles of Examples 3 and 4 thus make it possible to obtain a glossier and more sparkly make-up than the make-up of Example 5 obtained with aluminum powder, which is much more matte.

c) Light-transmission Test

On the same films used for the light-reflection test described above, each film was lit with a light beam oriented perpendicularly to the film (angle of 90° relative to the plane of the glass plate). The amount of light crossing through the film as a function of the angle was measured. The transmission "t" of the light was measured for the angle of −90° and the following arbitrary values were obtained:

| | |
|---|---|
| $t$=188.6 | Example 3 |
| $t$=114.9 | Example 4 |
| $t$=0 | Example 5 |

It is seen that the films of Examples 3 and 4 are good light transmitters and are not light-scattering, whereas the film of Example 5, which does not transmit light, is opaque.

What is claimed is:

1. A cosmetic make-up composition comprising at least one dyestuff in a cosmetically acceptable medium, wherein the at least one dyestuff comprises glass particles coated with at least one metallic coat*; and, the make-up composition further comprising at least one additional dyestuff different from the at least one dyestuff comprising glass particles coated with at least one metallic coat*.

2. The composition according to claim 1, wherein the at least one metallic coat is formed from at least one metal chosen from silver, nickel, chromium, molybdenum, aluminum, gold, copper, tin and magnesium.

3. The composition according to claim 1, wherein the at least one metallic coat is formed from at least one metal chosen from silver, nickel, chromium and molybdenum.

4. The composition according to claim 1, wherein the at least one metallic coat is present in an amount ranging from 0.1% to 50% by weight, relative to the total weight of the particles.

5. The composition according to claim 4, wherein the at least one metallic coat is present in an amount ranging from 1% to 20% by weight, relative to the total weight of the particles.

6. The composition according to claim 5, wherein the at least one metallic coat is present in an amount ranging from 2% to 8% by weight, relative to the total weight of the particles.

7. The composition according to claim 1, wherein the glass particles coated with the at least one metallic coat have an average size ranging from 1 μm to 500 μm.

8. The composition according to claim 7, wherein the glass particles coated with the at least one metallic coat have an average size ranging from 10 μm to 300 μm.

9. The composition according to claim 8, wherein the glass particles coated with the at least one metallic coat have an average size ranging from 25 μm to 150 μm.

10. The composition according to claim 1, wherein the glass particles coated with the at least one metallic coat have a thickness ranging from 0.1 μm to 25 μm.

11. The composition according to claim 10, wherein the glass particles coated with the metallic coat have a thickness ranging from 0.5 μm to 10 μm.

12. The composition according to claim 11, wherein the glass particles coated with the at least one metallic coat have a thickness ranging from 0.5 μm to 5 μm.

13. The composition according to claim 1, wherein the glass particles coated with the at least one metallic coat are present in an amount ranging from 0.1% to 90% by weight, relative to the total weight of the composition.

14. The composition according to claim 13, wherein the glass particles coated with the at least one metallic coat are present in an amount ranging from 1% to 30% by weight, relative to the total weight of the composition.

15. The composition according to claim 14, wherein the glass particles coated with the at least one metallic coat are present in an amount ranging from 2% to 10% by weight, relative to the total weight of the composition.

16. The composition according to claim 1, wherein the cosmetically-acceptable medium selected from at least one solvent and water.

17. The composition according to claim 16, wherein the at least one solvent is chosen from organic solvents.

18. The composition according to claim 1, wherein the cosmetically-acceptable medium is chosen from an aqueous-alcoholic mixture.

19. The composition according to claim 18, wherein the aqueous-alcoholic mixture comprises at least one $C_1$–$C_5$ monoalcohol.

20. The composition according to claim 17, wherein said organic solvents are liquid at room temperature and are chosen from ketones, alcohols, glycols, ethers, alkanes, cyclic aromatic compounds, and aldehydes.

21. The composition according to claim 17, wherein said organic solvents are liquid at room temperature and are chosen from propylene glycol ethers.

22. The composition according to claim 17, wherein said organic solvents are short-chain esters containing from 3 to 8 carbon atoms in total.

23. The composition according to claim 16, wherein the at least one solvent is present in an amount ranging from 30% to 99% by weight, relative to the total weight of the composition.

24. The composition according to claim 23, wherein the at least one solvent is present in an amount ranging from 60% to 90% by weight, relative to the total weight of the composition.

25. The composition according to claim 1, further comprising at least one film-forming polymer.

26. The composition according to claim 25, wherein said at least one film-forming polymer is dissolved in the cosmetically acceptable medium of the composition.

27. The composition according to claim 25, wherein said at least one film-forming polymer is dispersed in the form of particles in the cosmetically acceptable medium of the composition.

28. The composition according to claim 25, wherein the at least one film-forming polymer is chosen from radical-mediated polymers, polycondensates, and polymers of natural origin.

29. The composition according to claim 25, wherein the at least one film-forming polymer is chosen from vinyl polymers, vinyl copolymers, acrylic polymers, polyurethanes, polyurethane-acrylics, polyurethane-polyvinylpyrrolidones, polyester-polyurethanes, polyether-polyurethanes, polyureas, polyurea-polyurethanes, polyesters, polyesteramides, fatty-chain polyesters, polyamides, epoxyester resins, resins resulting from the condensation of formaldehyde with an arylsulphonamide, arylsulphonamide epoxy resins, shellac resins, sandaraque gums, dammar resins, elemis gums, copal resins and cellulose polymers.

30. The composition according to claim 29, wherein the cellulose polymers are chosen from nitrocelluloses, cellulose acetates, cellulose acetobutyrates, cellulose acetopropionates and ethylcelluloses.

31. The composition according to claim 25, wherein the at least one film-forming polymer is present in an amount ranging from 1% to 70% by weight, relative to the total weight of the composition.

32. The composition according to claim 31, wherein the at least one film-forming polymer is present in an amount ranging from 10% to 40% by weight, relative to the total weight of the composition.

[33. The composition of claim 1, further comprising at least one additional dyestuff, other than the at least one dyestuff comprising glass particles coated with the at least one metallic coat.]

34. The composition according to claim [33] *1*, wherein the at least one additional dyestuff is chosen from dyes and pulverulent dyestuffs.

35. The composition according to claim [33] *1*, wherein the at least one additional dyestuff is present in an amount ranging from 0.01% to 50% by weight, relative to the weight of the composition.

36. The composition according to claim 35, wherein the at least one additional dyestuff is present in an amount ranging from 0.01% to 30% by weight, relative to the weight of the composition.

37. The composition according to claim 1, further comprising at least one additive chosen from auxiliary film-forming agents, thickeners, filler, spreading agents, wetting agents, dispersants, anti-foaming agents, preserving agents, UV-screening agents, active agents, surfactants, moisturizers, fragrances, neutralizing agents, stabilizers, and antioxidants.

38. A nail varnish, a face powder, an eyeshadow, a foundation, a mascara, a make-up product for the lips, an eyeliner, or a make-up product for the bodycomprising[at least one dyestuff in a cosmetically acceptable medium, wherein the at least one dyestuff comprises], glass particles coated with at least one metallic coat*;*

*at least one dyestuff different from the glass particles coated with at least one metallic coat; and*

*a cosmetically acceptable medium.*

39. A process for [making up] *making-up* at least one keratin substance comprising applying at least one coat of a composition comprising glass particles coated with at least one metallic coat*, and at least one dyestuff different from the glass particles coated with at least one metallic coat,* to the at least one keratin substance to obtain a made-up keratin substance.

40. A process for making a composition for making-up at least one keratin substance comprising including in said composition glass particles coated with at least one metallic coat in an amount sufficient to impart a glossy and/or wear-resistant make-up*, and at least one dyestuff different from the glass particles coated with at least one metallic coat*.

41. A made-up support resulting from the application thereto of a make-up composition comprising glass particles coated with at least one metallic coat*, and at least one dyestuff different from the glass particles with at least one metallic coat*.

42. A made-up false nail, false eyelash, pastille, patch adhering to the skin or the lips, or a wig resulting from the application thereto of a make-up composition comprising glass particles coated with at least one metallic coat, *and at least one dyestuff different from the glass particles with at least one metallic coat*.

*43. A make-up product for the lips comprising:*

*glass particles coated with at least one metallic coat;*

*at least one dyestuff different from the glass particles coated with at least one metallic coat;*

*at least one film forming polymer;*

*at least one rheological agent;*

*at least one preserving agent; and*

*a cosmetically acceptable medium.*

*44. A method for making-up lips comprising applying to lips a cosmetic composition comprising:*

*glass particles coated with at least one metallic coat;*

*at least one dyestuff different from the glass particles coated with at least one metallic coat;*

*at least one film forming polymer;*

*at least one rheological agent;*

*at least one preserving agent; and*

*a cosmetically acceptable medium.*

*45. A mascara comprising:*

*glass particles coated with at least one metallic coat;*

*at least one dyestuff different from the glass particles coated with at least one metallic coat;*

*at least one preserving agent;*

*at least one filler; and*

*a cosmetically acceptable medium.*

*46. A method for making-up eyelashes comprising applying to eyelashes a cosmetic mascara composition comprising:*

*glass particles coated with at least one metallic coat;*

*at least one dyestuff different from the glass particles coated with at least one metallic coat;*

*at least one preserving agent;*

*at least one filler; and*

*a cosmetically acceptable medium.*

*47. A foundation comprising:*

*glass particles coated with at least one metallic coat,*

*at least one dyestuff different from the glass particles coated with at least one metallic coat;*

*at least one film forming polymer;*

*at least one filler; and*

*a cosmetically acceptable medium.*

*48. A method for making-up facial skin comprising applying to facial skin a cosmetic foundation composition comprising:*

*glass particles coated with at least one metallic coat;*

*at least one dyestuff different from the glass particles coated with at least one metallic coat;*

*at least one film forming polymer;*

*at least one filler; and*

*a cosmetically acceptable medium.*

*49. A nail varnish comprising:*

*glass particles coated with at least one metallic coat;*

*at least one dyestuff different from the glass particles coated with at least one metallic coat;*

*at least one film forming polymer;*

*at least one rheological agent; and*

*a cosmetically acceptable medium.*

*50. A method for making-up nails comprising applying to nails a cosmetic varnish composition comprising:*

*glass particles coated with at least one metallic coat;*

*at least one dyestuff different from the glass particles coated with at least one metallic coat;*

*at least one film forming polymer;*

*at least one rheological agent; and*

*a cosmetically acceptable medium.*

*51. A method for making-up eyelashes comprising applying to eyelashes a cosmetic mascara composition comprising:*

*glass particles coated with at least one metallic coat;*

*at least one dyestuff different from the glass particles coated with at least one metallic coat;*

*at least one preserving agent;*

*at least one film-forming polymer; and*

*a cosmetically acceptable medium.*

* * * * *

UNITED STATES PATENT AND TRADEMARK OFFICE

CERTIFICATE OF CORRECTION

PATENT NO. : RE42,260 E
APPLICATION NO. : 10/919516
DATED : March 29, 2011
INVENTOR(S) : Roland Ramin et al.

It is certified that error appears in the above-identified patent and that said Letters Patent is hereby corrected as shown below:

Claim 16, col. 9, line 20, “medium selected from” should read --medium is chosen from--.

Signed and Sealed this
Fourteenth Day of June, 2011

David J. Kappos

David J. Kappos
*Director of the United States Patent and Trademark Office*